(12) United States Patent
Zhang et al.

(10) Patent No.: US 11,519,827 B2
(45) Date of Patent: Dec. 6, 2022

(54) TEST STRIP PROCESS DEVICE

(71) Applicant: NANJING LIMING BIO-PRODUCTS CO., LTD., Jiangsu (CN)

(72) Inventors: Shuwen Zhang, Jiangsu (CN); Guangming Liu, Jiangsu (CN); Xiang Huang, Jiangsu (CN); Luanyan Sun, Jiangsu (CN); Xiaoliang Wang, Jiangsu (CN)

(73) Assignee: NANJING LIMING BIO-PRODUCTS CO., LTD., Jiangsu (CN)

( * ) Notice: Subject to any disclaimer, the term of this patent is extended or adjusted under 35 U.S.C. 154(b) by 0 days.

(21) Appl. No.: 17/746,552

(22) Filed: May 17, 2022

(65) Prior Publication Data
US 2022/0276131 A1 Sep. 1, 2022

Related U.S. Application Data

(63) Continuation of application No. PCT/CN2020/130303, filed on Nov. 20, 2020.

(30) Foreign Application Priority Data

Nov. 11, 2020 (CN) .......................... 202022594375.9

(51) Int. Cl.
*G01N 1/02* (2006.01)
*B01L 3/00* (2006.01)
(Continued)

(52) U.S. Cl.
CPC ................ *G01N 1/02* (2013.01); *B01L 3/502* (2013.01); *A61B 10/0045* (2013.01);
(Continued)

(58) Field of Classification Search
CPC .... G01N 1/02; G01N 2001/028; B01L 3/502; B01L 2400/0644; A61B 10/0045; A61B 10/02
See application file for complete search history.

(56) References Cited

U.S. PATENT DOCUMENTS 6,248,294 B1   6/2001 Nason

FOREIGN PATENT DOCUMENTS

| CN | 207851010 U | 9/2018 |
|---|---|---|
| CN | 210400888 U | 4/2020 |

(Continued)

OTHER PUBLICATIONS

International Search Report and Written Opinion cited in PCT/CN2020/130303 dated Aug. 10, 2021, 10 pages.

*Primary Examiner* — Samuel P Siefke
(74) *Attorney, Agent, or Firm* — Cooper Legal Group, LLC

(57) ABSTRACT

The present application relates to a test strip process device. The test strip process device includes an inner cylinder, an outer cylinder, a mounting cover and a liquid supply assembly. One end of the outer cylinder is open, and the other end of the outer cylinder is closed. Both ends of the inner cylinder are open, and the inner cylinder is located in the outer cylinder. An end of the inner cylinder away from the open end of the outer cylinder is hermetically connected to the inner side wall of the outer cylinder, and a test strip chamber is formed between an outer peripheral wall of the inner cylinder and an inner peripheral wall of the outer cylinder. The mounting cover is detachably connected to an end wall of the open end of the outer cylinder, and the liquid supply assembly is provided on the mounting cover.

6 Claims, 11 Drawing Sheets

Figure 1:
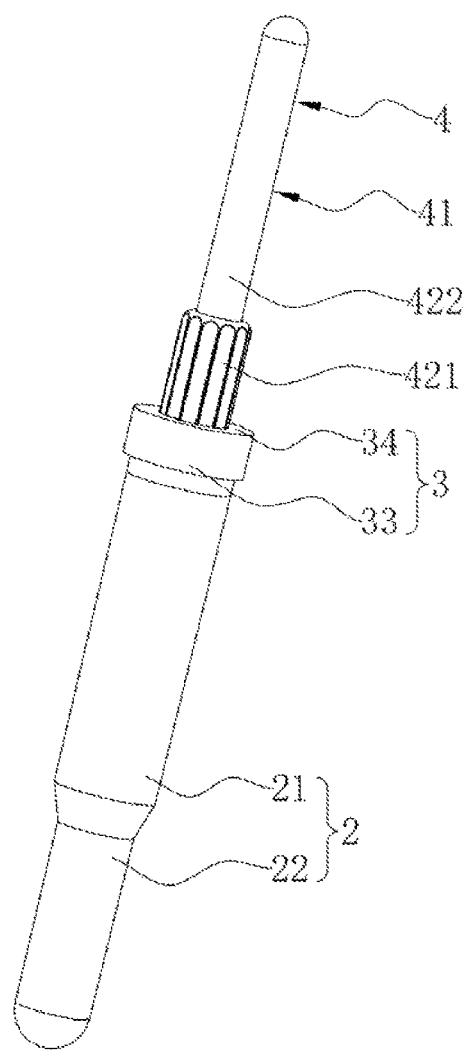

(51) Int. Cl.
*A61B 10/00* (2006.01)
*A61B 10/02* (2006.01)

(52) U.S. Cl.
CPC ....... *A61B 10/02* (2013.01); *B01L 2400/0644* (2013.01); *G01N 2001/028* (2013.01)

(56) References Cited

FOREIGN PATENT DOCUMENTS

| | | |
|---|---|---|
| CN | 210774757 U | 6/2020 |
| CN | 210774762 U | 6/2020 |
| CN | 211402158 U | 9/2020 |

A-A

C-C

TEST STRIP PROCESS DEVICE

CROSS-REFERENCE TO RELATED APPLICATION

This application is a continuation of PCT application serial no. PCT/CN2020/130303, filed on Nov. 20, 2020, which claims the priority and benefit of Chinese patent application serial no. 202022594375.9, filed on Nov. 11, 2020. The entireties of PCT application serial no. PCT/CN2020/130303 and Chinese patent application serial no. 202022594375.9 are hereby incorporated by reference herein and made a part of this specification.

FIELD OF THE INVENTION

The present application relates to the field of disease detection, and particularly to a test strip process device.

BACKGROUND

Novel coronavirus (COVID-19) is a new coronavirus strain with highly contagious, which may cause fevers, coughing, difficulty in breathing and even death in infected people.

The infected people infected with the COVID-19 may have main clinical manifestation such as fever, fatigue, dry cough, even hypoxia, but less symptoms of upper respiratory such as nasal congestion and runny nose. After infected with pneumonia, about half of the patients may develop dyspnea after one week, and the severe may rapidly progress to acute respiratory distress syndrome, septic shock, uncorrectable metabolic acidosis and coagulation dysfunction. At present, the screening of COVID-19 need to be conducted in combination with clinical symptoms, the results of blood routine, CT examination or nucleic acid examination.

However, there may still exist detection inaccuracy in the related technologies, which will bring serious problems to the detection of the COVID-19. Therefore, there is still need for improving the detection accuracy of COVID-19.

BRIEF SUMMARY OF THE INVENTION

In order to improve the detection accuracy of COVID-19, the present application provides a test strip process device.

The technical solution of the test strip process device provided in the present application is as follows:

a test strip process device includes an inner cylinder, an outer cylinder, a mounting cover and a liquid supply assembly, wherein one end of the outer cylinder is open, and the other end of the outer cylinder is closed, both ends of the outer cylinder are open, and the inner cylinder is located in the outer cylinder. The end of the inner cylinder away from the open end of the outer cylinder is hermetically connected to the inner side wall of the outer cylinder, and a test strip chamber is formed between an outer peripheral wall of the inner cylinder and an inner peripheral wall of the outer cylinder. The mounting cover is detachably connected to an end wall of the open end of the outer cylinder, and the liquid supply assembly is provided on the mounting cover.

By adopting the above technical solution, the treatment liquid can flow into the inner cylinder from the liquid supply assembly and then into the end of outer cylinder away from the open end through the inner side wall of the inner cylinder, so that the treatment liquid can react with the virus. Then, inverting the outer cylinder, the virus-adsorbed treatment liquid may flow into the test strip chamber. At this time, the test strip located in the test strip chamber may contact with the virus-adsorbed treatment liquid, so that the virus-adsorbed treatment liquid can react with the test strip to obtain test results. Further, in the present application, the end of the inner cylinder away from the open end of the outer cylinder is hermetically connected to the outer cylinder, so that the treatment liquid would not leak from the connection part between the inner cylinder and the outer cylinder during the process that the treatment liquid flows into the side of the outer cylinder away from the open end, to reduce pollution of the test strip. During the process that the virus-adsorbed treatment liquid flows into the test paper chamber, the virus-adsorbed treatment liquid also would not leak from the connection part between the inner cylinder and the outer cylinder, and smoothly contact with the end of the test strip at the mounting cover, so that the test strip can normally react with the virus-adsorbed treatment liquid. Therefore, the present application can improve the accuracy of virus detection.

Alternatively, the end of the inner cylinder away from the open end of the outer cylinder is integrally connected to an inner side wall of the outer cylinder.

By adopting the above technical solution, it can be directly and effectively achieved that the end of the inner cylinder away from the open end of the outer cylinder can hermetically connected to the outer cylinder. The inner cylinder and the outer cylinder are integrally formed, so that the processing is more convenient and faster.

Alternatively, the outer cylinder includes a testing barrel and a reaction barrel, the reaction barrel is connected to one end of the testing barrel, one end of the inner cylinder is hermetically connected to the reaction barrel, a connection side of an inner wall of the inner cylinder and an inner wall of the reaction barrel form a smooth surface, a test strip chamber is formed between the inner cylinder and the testing barrel, and the mounting cover is mounted at one end of the testing barrel away from the reaction barrel.

By adopting the above technical solution, the test strip chamber formed between the inner cylinder and the testing barrel may be used to accommodate the test strip for testing, and the reaction barrel provides a chamber for the reaction between the virus and the treatment liquid. A connection side of an inner wall of the inner cylinder and an inner wall of the reaction barrel form a smooth surface, so that connecting end of the inner cylinder and the reaction barrel can transition smoothly when connected. Further, the treatment liquid and the virus-adsorbed treatment liquid can flow smoothly between the inner cylinder and the reaction barrel, thereby the residue of the treatment liquid on the peripheral wall of the inner cylinder can be reduced, and the treatment liquid can be adequately reacted with the virus. Meanwhile, the residue of the virus-adsorbed treatment liquid on the peripheral walls of the reaction barrel and the inner cylinder can be reduced, so that the virus-adsorbed treatment liquid can adequately react with the test strip to improve the detection accuracy.

Optionally, the mounting cover includes a connection wall and a mounting wall, and the mounting wall is integrally connected to one end wall of connection wall. The connection wall of the mounting cover is connected to the open end of the outer cylinder, and a gap is formed between an end wall of the inner cylinder towards the open end of the outer cylinder and the mounting wall of the mounting cover.

By adopting the above technical solution, the inner cylinder is communicated with the test strip chamber, such that the virus-adsorbed treatment liquid can fully flow throughout the test strip chamber through the gap between the inner cylinder and the mounting cover after flowing to the position of the mounting cover, therefore, the virus-adsorbed treatment liquid can adequately react with the test strip.

Optionally, a plurality of isolation strips are provided on the outer peripheral wall of the inner cylinder and/or the inner peripheral wall of the outer cylinder towards the inner cylinder.

By adopting the above technical solution, an isolation chamber is formed between the adjacent isolation strips, and the test strips are located in the corresponding isolation chamber, so that the interaction between test strips can be reduced, each test strip can adequately react with the virus-adsorbed treatment liquid to improve the detection accuracy.

Optionally, the isolation strip is connected to the outer peripheral wall of the inner cylinder or the inner peripheral wall of the outer cylinder towards the inner cylinder, and the end of the isolation strip away from the connecting end is a movable end.

By adopting the above technical solution, the end of the isolation strip away from the connecting end is a movable end, when putting a test strip, the test strip may be allowed to be inserted into part of the movable end of the isolation strip, thereby reducing the damage caused by direct impact of the test strip on the isolation strip.

Optionally, a gap is formed between the end wall of the isolation strip towards the mounting cover and the end wall of the open end of the outer cylinder.

By adopting the above technical solution, a chamber is formed between a part of the outer cylinder close to the open end and without the isolation strip and the outer peripheral wall of the inner cylinder, and the test strip can relatively freely move in the chamber, so that the chamber can provide a space for test strip to adjust the test strip at the position opposite to the two isolation strips, and the operation is more convenient and quicker.

Optionally, the distance between the movable end and the connecting end of the isolation strip is gradually decreased along the direction towards the mounting cover, and the width of the isolation strip is gradually decreased along the direction towards the mounting cover.

By adopting the above technical solution, the distance between the movable end and the connecting end of the isolation strip is gradually decreased along the direction towards the mounting cover, so that the test strip can be inserted into the movable end more under allowable conditions. Meanwhile, the frictional force on the test strip increases gradually, which can further reduce the damage of the isolation strip while reducing the further misinsertion of the isolation strip. Further, the width of the isolation strip is gradually decreased along the direction towards the mounting cover, such that the test strip inserting end formed between the adjacent isolation strips is bigger, then the insertion of test strip is convenient.

Optionally, the liquid supply assembly includes a liquid guiding tube and a liquid storage component, the liquid guiding tube is provided on the mounting cover, one end of the liquid guiding tube extends into the inner cylinder, a distance between the outer peripheral wall of the liquid guiding tube and the inner peripheral wall of the inner cylinder is 0.75-2 mm, the liquid storage component is provided at one end of the liquid guiding tube away from the inner cylinder, and the liquid storage component is used for storing the treatment liquid.

By adopting the above technical solution, the liquid guiding tube extends into the inner cylinder, so that the liquid in the liquid storage component may smoothly flow into the reaction barrel through the inside of the inner cylinder. The distance between the liquid guiding tube and the inner peripheral wall of the inner cylinder is 0.75-2 mm, so that the virus-adsorbed treatment liquid can smoothly flow into the test strip chamber.

Optionally, the side of the mounting wall of the mounting cover towards the inner cylinder is provided with a sealing ring, an outer diameter of the sealing ring gradually decreases along the direction away from the mounting cover, an outer diameter of the sealing ring at the end away from the mounting cover is less than the inner diameter of the outer cylinder, and an outer diameter of the sealing ring at the end close to the mounting cover is greater than the inner diameter of the outer cylinder, and the outer peripheral wall of the sealing ring abuts against the inner peripheral wall of the open end of the outer cylinder.

By adopting the above technical solution, during the process of mounting the mounting cover to the outer cylinder, the sealing ring is inserted into the outer cylinder. As the inner cylinder and the mounting cover are buckled with each other, the inner peripheral wall of the outer cylinder gradually abuts against the sealing ring, the sealing ring is deformed inward, so that the outer wall of the sealing ring abuts against the inner peripheral wall of the open end of the outer cylinder, so as to realize the sealing between the mounting cover and the outer cylinder. Therefore, the leakage of treatment solution can be reduced, the detection accuracy can be improved, further, the leakage of virus and the occurrence of secondary infection also can be reduced.

BRIEF DESCRIPTION OF THE DRAWINGS

FIG. 1 shows a structural schematic diagram of a test strip process device according to an embodiment of the present application.

FIG. 2 shows a top view of a test strip process device according to an embodiment of the present application.

FIG. 3 shows a cross-sectional view taken along line A-A in FIG. 2.

FIG. 4 shows an enlarged view at B in FIG. 3.

FIG. 5 shows a structural schematic diagram of a mounting cover according to an embodiment of the present application.

FIG. 6 shows a structural schematic diagram of an outer cylinder according to an embodiment of the present application.

FIG. 7 shows a structural schematic diagram of an isolation strip according to an embodiment of the present application.

FIG. 8 shows a top view of a test strip process device according to another embodiment of the present application.

FIG. 9 shows a cross-sectional view taken along line C-C in FIG. 7.

FIG. 10 shows a top view of a test strip process device according to still another embodiment of the present application.

FIG. 11 shows a cross-sectional view taken along line D-D of FIG. 10.

DETAILED DESCRIPTION

The present application is further described in detail in combination with FIGS. 1-11 below.

As shown in FIG. 1, in some embodiments, a test strip process device mainly including an outer cylinder 2, a mounting cover 3 and a liquid supply assembly 4 is provided.

Figure 2:
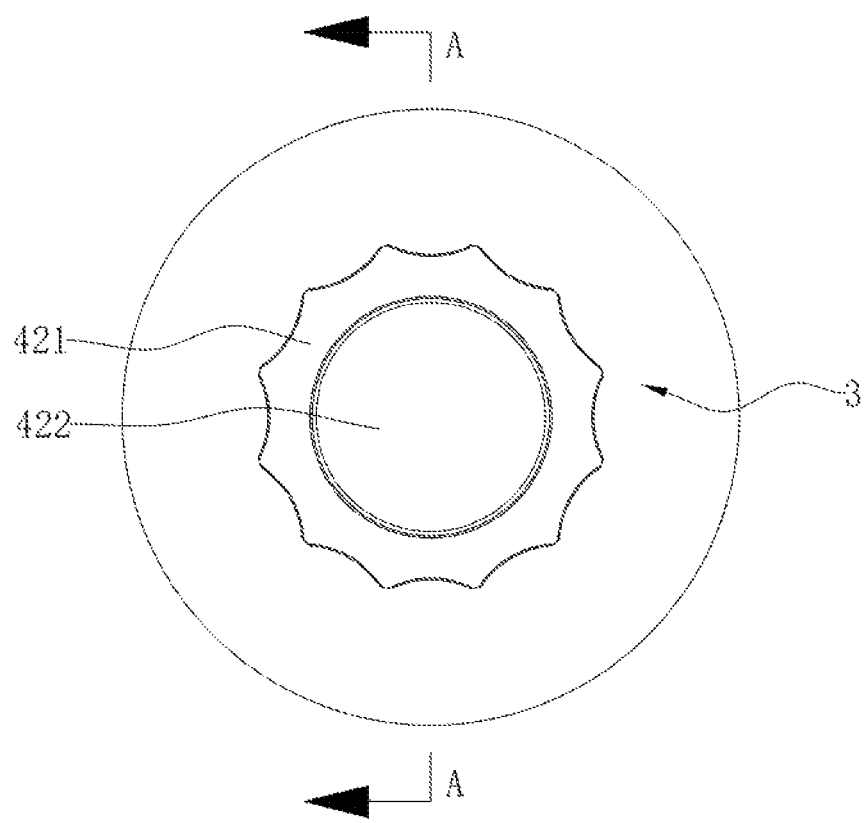
Figure 3:
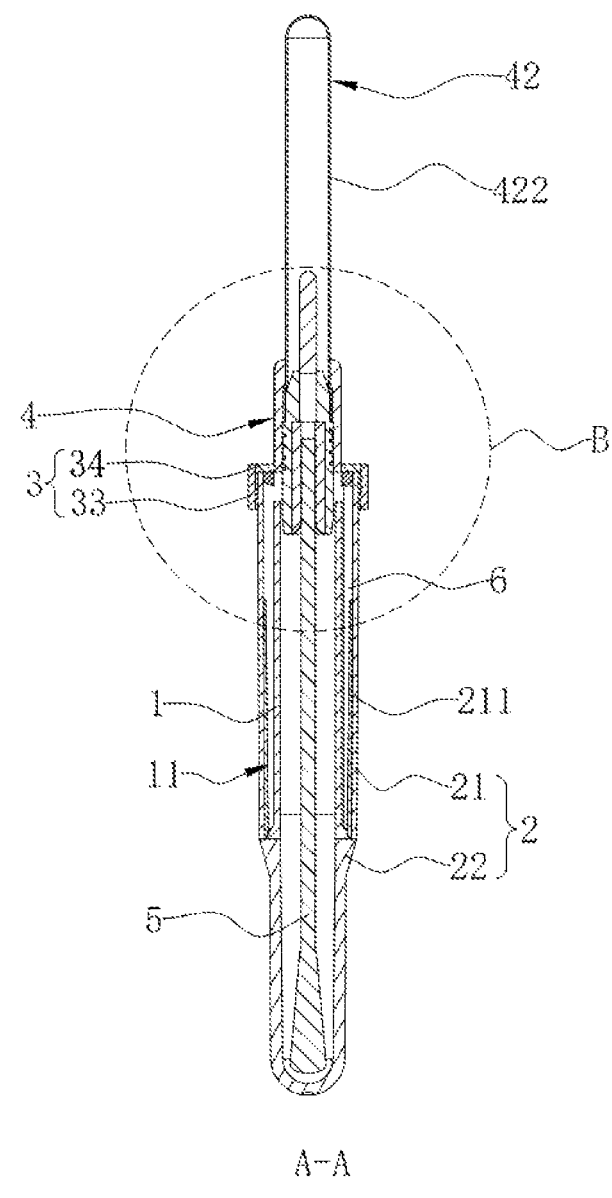

As shown in FIGS. 2-3, the test strip process device also includes inner cylinder 1. In some embodiments, the outer cylinder 2 includes a testing barrel 21 and a reaction barrel 22. The testing barrel 21 and the reaction barrel 22 are all circular cylinder, both ends of the testing barrel 21 are provided with opening, and one end of the reaction barrel 22 is open, the other end is closed. One end of the testing barrel 21 is integrally connected to the end wall of the open end of the reaction barrel 22. The inner cylinder 1 is located in the testing barrel 21, one end is integrally connected to the end wall of the open end of the reaction barrel 22, and a test strip chamber 11 is formed between the inner cylinder 1 and the testing barrel 21. Meanwhile, an inner diameter of the inner cylinder 1 is same as the inner diameter of the reaction barrel 22, so that an inner peripheral wall of a connection side of the inner cylinder 1 and a reaction barrel 22 form a smooth surface.

Figure 4:
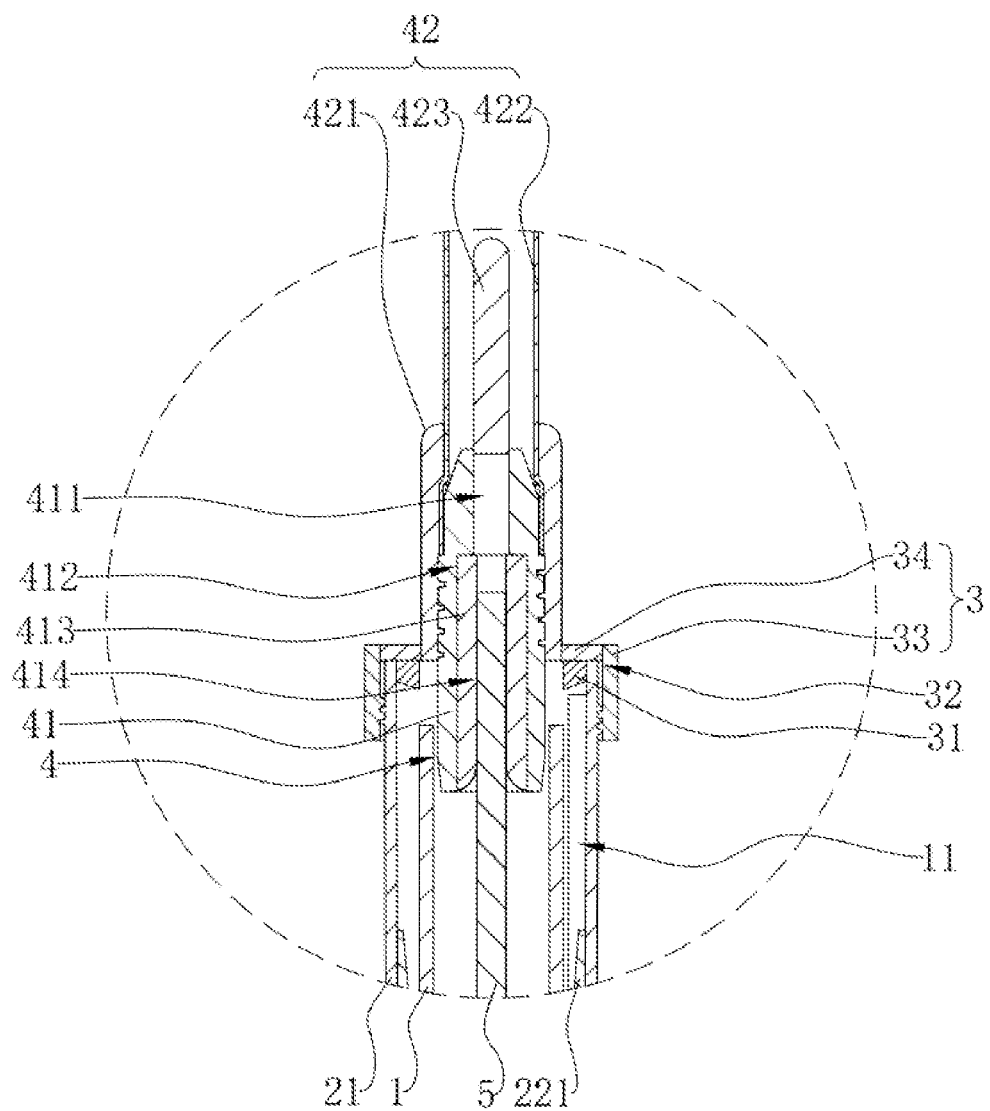

As shown in FIGS. 3-4, in some embodiments, the mounting cover 3 is a soft plastic cover and includes a ring connection wall 33 and a circular mounting wall 34, and the mounting wall 34 is integrally connected between one axial end wall of the mounting wall 34. The connection wall 33 of the mounting cover 3 is threaded to an outer wall of one end of the testing barrel 21 away from the reaction barrel 22. The thread of outer peripheral wall of the testing barrel 21 is segmented thread. A gap is formed between one end of the inner cylinder 1 away from the reaction barrel 22 and the mounting wall 34 of the mounting cover 3. The liquid supply assembly 4 is provided on the mounting wall 34 of the mounting cover 3 and used for transporting the treatment liquid to the inner cylinder 1.

Figure 5:
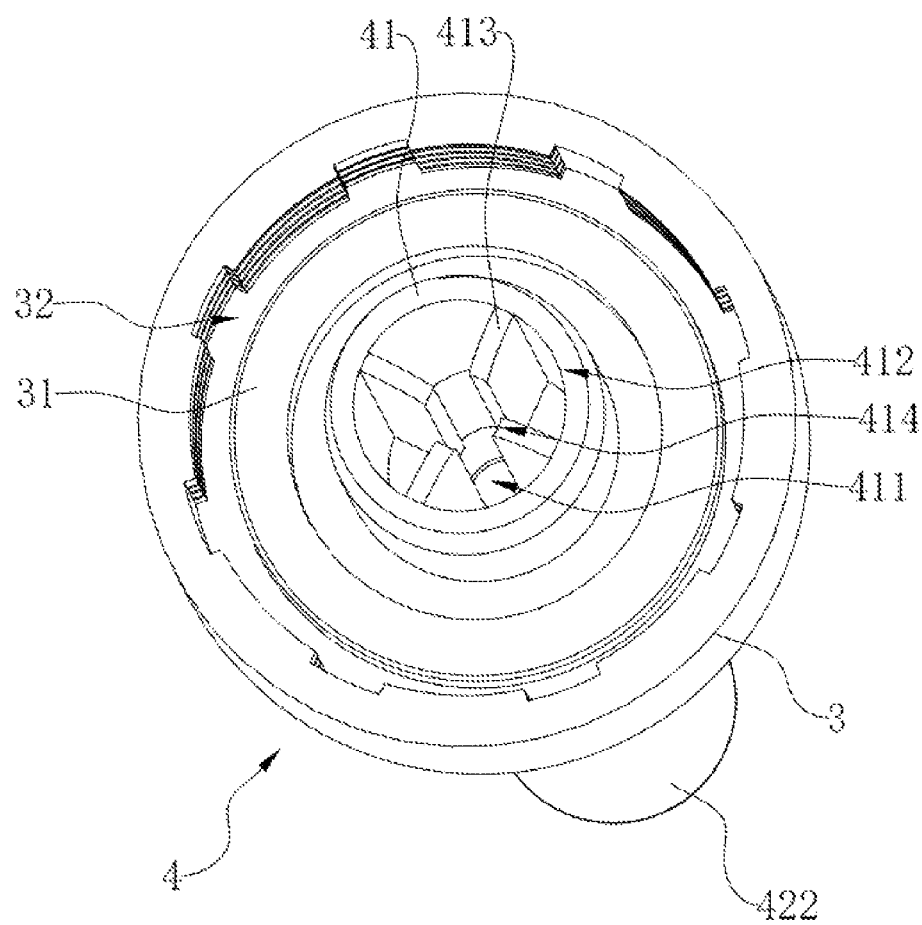
Figure 6:
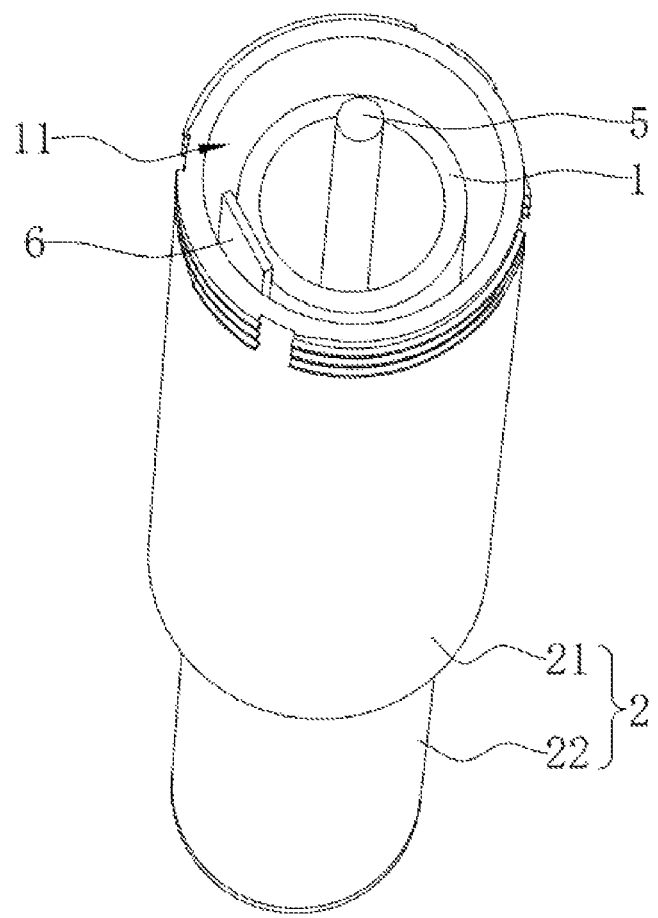

As shown in FIGS. 4-5, in some embodiments, the liquid supply assembly 4 includes a liquid guiding tube 41 and a liquid storage component 42 including a snap connection tube 421, a liquid storage tube 422 and a plugging rod 423. The snap connection tube 421 is a circular cylinder provided with openings at two ends, and one end of which is fixedly connected to the mounting wall 34 of the mounting cover 3 along its length direction. The snap connection tube 421 is communicated with the mounting cover 3, the liquid guiding tube 41 is threaded to the inner peripheral wall of the snap connection tube 421, and the outer peripheral wall of the liquid guiding tube 41 is hermetically connected to the inner peripheral wall of the snap connection tube 421. A through groove 411 used for flowing the treatment liquid is provided in the liquid guiding tube 41, and one end of the liquid guiding tube 41 extends into the inner cylinder 1. The distance between the outer peripheral wall of the liquid guiding tube 41 and the inner peripheral wall of the inner cylinder 1 is 0.75-2 mm. In some embodiments, the distance between the outer peripheral wall of the liquid guiding tube 41 and the inner peripheral wall of the inner cylinder 1 is 0.8 mm. A fixed groove 412 is also provided at one end of the liquid guiding tube 41 extended into the inner cylinder 1, which is communicated with the through groove 411. Four clamping blocks 413 are fixedly connected to the groove wall of the fixed groove 412, and a clamping groove 414 is formed between opposite end walls of the four clamping blocks 413.

As shown in FIG. 4, the liquid storage tube 422 is a circular hose with one end closed, the open end of the liquid storage tube 422 is inserted into the end of the snap connection tube 421 away from the mounting cover 3. The liquid storage tube 422 is located between the snap connection tube 421 and the liquid guiding tube 41, and the outer peripheral wall of the liquid guiding tube 41 and the inner peripheral wall of the snap connection tube 421 hermetically abuts against the liquid storage tube 422. The plugging rod 423 is inserted into the groove wall of the through groove 411 of the liquid guiding tube 41 to seal the through groove 411 of the liquid guiding tube 41. The treatment liquid is contained in the liquid storage tube 422. In some embodiments, the treatment liquid is eluent.

When testing the virus, a sampling tool 5 such as a cotton swab is used for sampling. Then, the end of the sampling tool 5 away from the sampling end is inserted between the four clamping blocks 413. A test strip 6 is put into the test strip chamber 11, and the mounting cover 3 is threaded to the testing barrel 21, at this time, the sampling end of the sampling tool 5 with virus sample is located in the reaction barrel 22. The liquid storage tube 422 is bent, so that the plugging rod 423 is broken out from the groove wall of the through groove 411, so that the treatment liquid in the liquid storage tube 422 enters into the inner cylinder 1 along the through groove 411 and the fixed groove 412 downward until the treatment liquid enters into the reaction barrel 22 and contacts with the sampling end of the sampling tool 5. The reaction barrel 22 is shaken, so that the virus sample is fully dispersed in the treatment liquid. Finally, inverting the reaction barrel 22 and the testing barrel 21, the virus-adsorbed treatment liquid flows along the inner cylinder 1 and then through the gap between the outer peripheral wall of the liquid guiding tube 41 and the inner peripheral wall of the inner cylinder 1 to the mounting cover 3. Then, the virus-adsorbed treatment liquid flows to the test strip chamber 11 through the gap between the inner cylinder 1 and the mounting cover 3, so that the test strip 6 can contact and react with the virus-adsorbed treatment liquid to test the virus.

As shown in FIGS. 4-5, in order to improve the tightness between the mounting cover 3 and the testing barrel 21, in some embodiments, a sealing ring 31 is fixedly connected to the side of the mounting wall 34 of the mounting cover 3 towards the inner cylinder 1. The sealing ring 31 may be a soft plastic ring. In some embodiments, an outer diameter of the sealing ring 31 gradually decreases along the direction away from the mounting cover 3, an outer diameter of the end of the sealing ring 31 away from the mounting cover 3 is less than the inner diameter of the outer cylinder 2, and an outer diameter of the end of the sealing ring 31 close to the mounting cover 3 is greater than the inner diameter of the outer cylinder 2. A sealing inserting groove 32 is formed between the outer peripheral wall of the sealing ring 31 and inner peripheral wall of the mounting cover 3. When the mounting cover 3 is threaded to the testing barrel 21, the sealing ring 31 is gradually inserted into the testing barrel 21. As the mounting cover 3 continue to screw on the testing barrel 21, the inner peripheral wall of the testing barrel 21 begins to squeeze the sealing ring 31, then the sealing ring 31 will deform to a certain extent, so that the outer peripheral wall of the sealing ring 31 abuts against the inner peripheral wall of the open end of the outer cylinder 2, and the mounting cover 3 is hermetically connected to the testing barrel 21.

Figure 7:
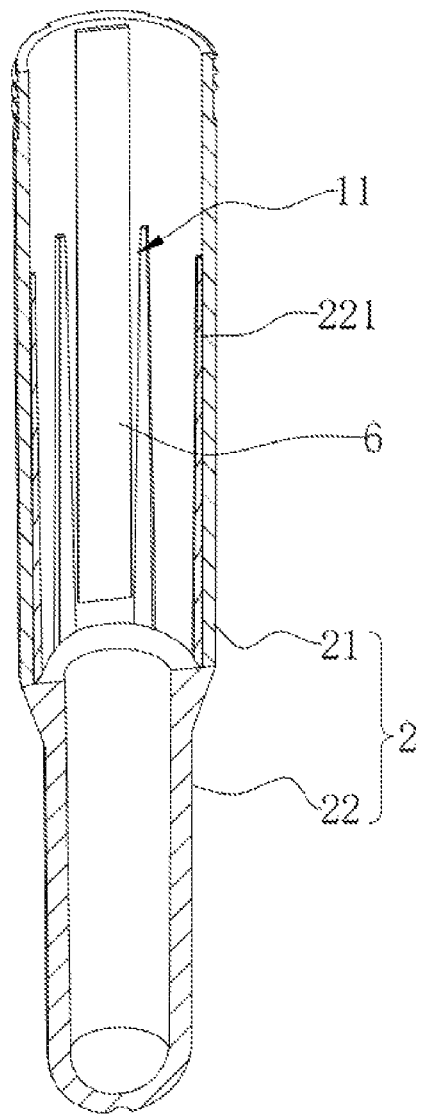

As shown in FIG. 7, in order to reduce the stacking of test strips 6 in the test strip chamber 11, which may affect the detection effect, a plurality of isolation strips 221 is fixedly connected to the inner peripheral wall of the testing barrel 21. In some embodiments, the isolation strip 221 is evenly distributed on the inner peripheral wall of the testing barrel 21 along its axial direction, and a gap is formed between a movable end of the isolation strip 221 away from the testing barrel 21 and the outer peripheral wall of the inner cylinder 1. Note that the gap between the movable end of the isolation strip 221 and the outer peripheral wall of the inner cylinder 1 is less than the thickness of the test strip 6, and a gap is formed between the end wall of the isolation strip 221 towards the mounting cover 3 and the end wall of the open end of the outer cylinder 2, that is, the isolation strip 221 does not cover the testing barrel 21 along the length direction of the testing barrel 21. In this way, when mounting the test strip 6, firstly, the test strip 6 is inserted into the test strip chamber 11 without the isolation strip 221, then, the test strip 6 is aligned with and inserted into the gap formed between the adjacent isolation strips 221, so that the test strip 6 can be relatively independently mounted into the test strip chamber 11.

In some embodiments, the implementation principle of the test strip process device is that, when testing the virus, the sampling tool 5 is used for sampling. Then, the end of the sampling tool 5 away from its sampling end is inserted between the four clamping blocks 413.

The test strip 6 is then put into the test strip chamber 11, so that the test strip 6 is inserted into two adjacent isolation strips 211. Then, the mounting cover 3 is threaded to the testing barrel 21, so that the outer peripheral wall of the sealing ring 31 abuts against the inner peripheral wall of the open end of the outer cylinder 2, and the mounting cover 3 is hermetically connected to the testing barrel 21, at this time, the sampling end of the sampling tool 5 with virus sample is located in the reaction barrel 22.

The liquid storage tube 422 is bent so that the plugging rod 423 is broken out from the through groove 411, meanwhile, the through groove 411 is opened, the treatment liquid in the liquid storage tube 422 flows into the reaction barrel 22 and contacted with the sampling end of the sampling tool 5. Then, the reaction barrel 22 is shaken, so that the virus sample is fully dispersed in the treatment liquid.

Finally, inverting the reaction barrel 22 and the testing barrel 21, the virus-adsorbed treatment liquid flows to the test strip chamber 11 through the gap between the inner cylinder 1 and the mounting cover 3, so that the test strip 6 can contact and react with the virus-adsorbed treatment liquid, so as to test the virus.

Figure 8:
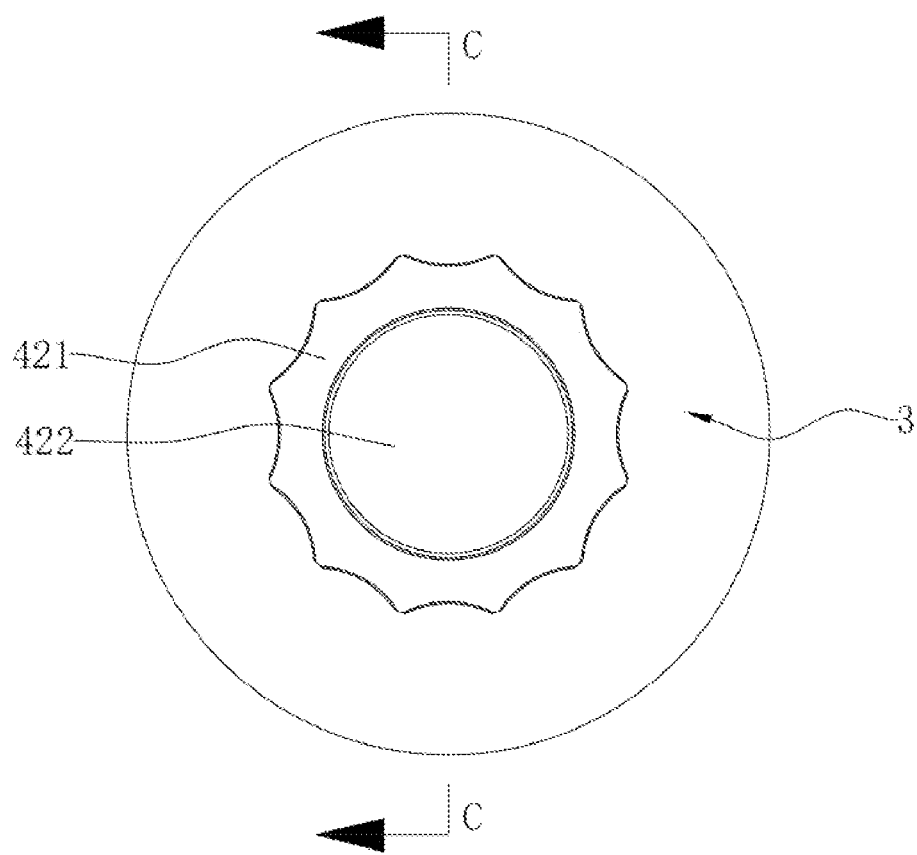
Figure 9:
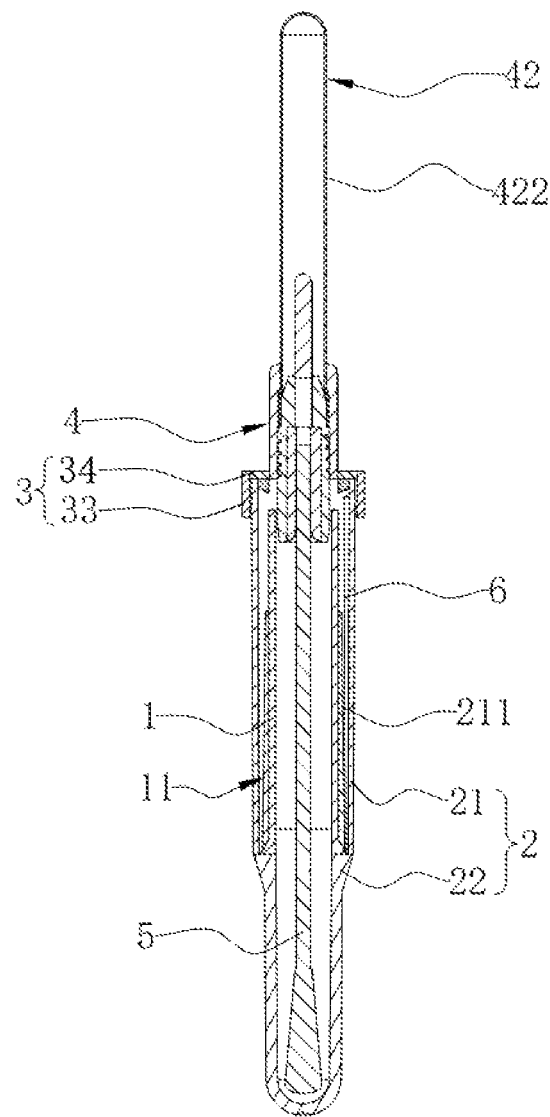

As shown in FIGS. 8-9, in some embodiments, the isolation strip 221 is fixedly connected to the outer peripheral wall of the inner cylinder 1, a gap is formed between a movable end of the isolation strip 221 away from the inner cylinder 1 and the peripheral wall of the outer cylinder 2, and the test strip 6 is located between the isolation strip 221 and the outer cylinder 2.

Figure 10:
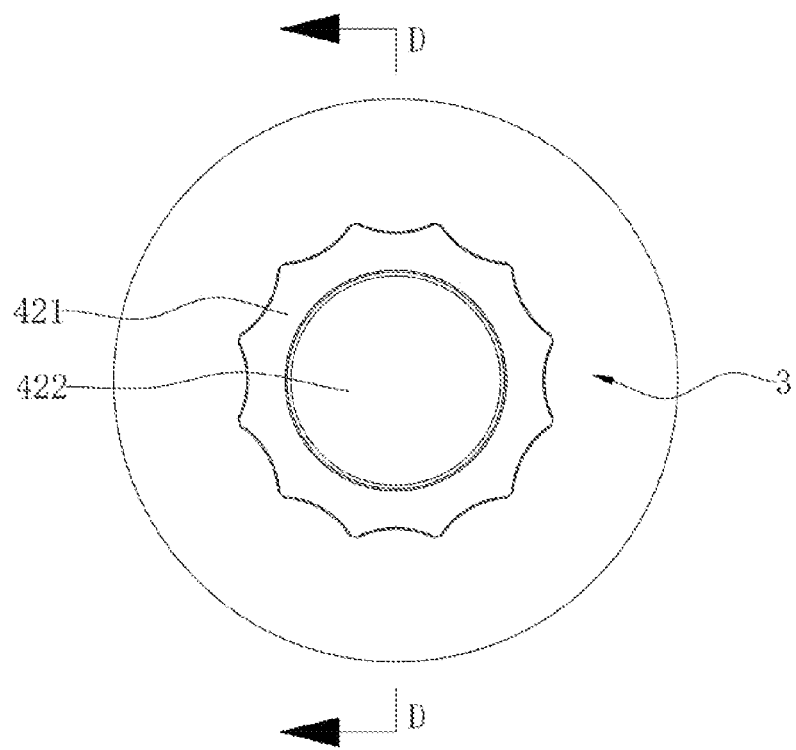
Figure 11:
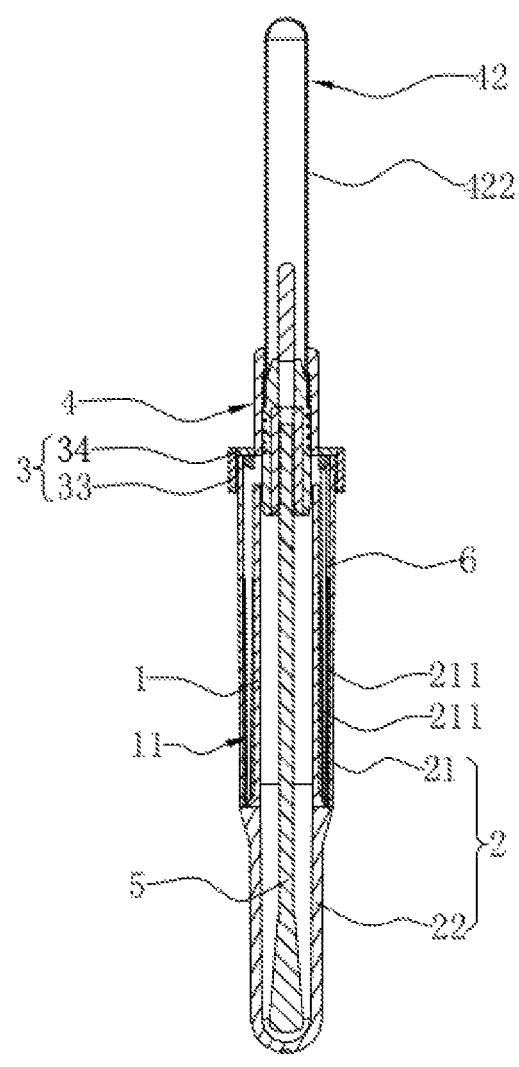

As shown in FIGS. 10-11, in some embodiments, the outer peripheral wall of the inner cylinder 1 and the inner peripheral wall of the outer cylinder 2 are both fixedly connected to the isolation strip 221, the movable end of the isolation strip 221 on the outer cylinder 2 is opposite to the movable end of the isolation strip 221 on the inner cylinder 1, and a gap is formed between the movable end of the isolation strip 221 on the outer cylinder 2 and the movable end of the isolation strip 221 on the inner cylinder 1. The test strip 6 is located between the movable end of the isolation strip 221 on the outer cylinder 2 and the movable end of the isolation strip 221 on the inner cylinder 1.

The test strip process device in the present application can specifically be used for testing pathogenic pathogen antigens, antibodies and nucleic acids, tumor markers, allergies (allergens), proteins, enzymes, autoantibodies and other physiological and biochemical or immune function indicators, and can also be used for microbial identification or susceptibility testing.

The above are preferred embodiments of the present application, which are not intended to limit the protection scope of the present application. Therefore, all equivalent changes made according to the structure, shape and principle of the present application should be within the protection scope of the present application.

What is claimed is:

1. A test strip process device, comprising an inner cylinder, an outer cylinder, a mounting cover and a liquid supply assembly, wherein one end of the outer cylinder is open, a second end of the outer cylinder is closed, both ends of the inner cylinder are open, the inner cylinder is located in the outer cylinder, an end of the inner cylinder away from the one end of the outer cylinder is hermetically connected to an inner side wall of the outer cylinder, a test strip chamber is defined between an outer peripheral wall of the inner cylinder and an inner peripheral wall of the outer cylinder, the mounting cover is detachably connected to an end wall of the one end of the outer cylinder, and the liquid supply assembly is provided on the mounting cover;

wherein the end of the inner cylinder away from the one end of the outer cylinder is integrally connected to the inner side wall of the outer cylinder;

wherein the outer cylinder comprises a testing barrel and a reaction barrel, the reaction barrel is connected to one end of the testing barrel, one end of the inner cylinder is hermetically connected to the testing barrel, an inner wall of the inner cylinder and an inner wall of the outer cylinder form a smooth surface, the test strip chamber is formed between the inner cylinder and the testing barrel, and the mounting cover is mounted at an end of the testing barrel away from the reaction barrel;

wherein the mounting cover comprises a connection wall and a mounting wall, the mounting wall is integrally connected to an end wall of the connection wall at one end, the connection wall of the mounting cover is connected to the one end of the outer cylinder, and a gap is formed between an end wall of the inner cylinder towards the one end of the outer cylinder and the mounting wall of the mounting cover;

wherein a second gap is formed between one end of the inner cylinder away from the reaction barrel and the mounting wall of the mounting cover;

wherein the liquid supply assembly comprises a liquid guiding tube and a liquid storage component, the liquid guiding tube is provided on the mounting cover, one end of the liquid guiding tube extends into the inner cylinder, a distance between an outer peripheral wall of the liquid guiding tube and an inner peripheral wall of the inner cylinder is 0.75-2 mm, the liquid storage component is provided at a second end of the liquid guiding tube away from the inner cylinder, and the liquid storage component is configured for storing treatment liquid.

2. The test strip process device according to claim 1, wherein a plurality of isolation strips are provided on at least one of the outer peripheral wall of the inner cylinder or the inner peripheral wall of the outer cylinder towards the inner cylinder.

3. The test strip process device according to claim 2, wherein each of the isolation strips is connected to the outer peripheral wall of the inner cylinder and the inner peripheral wall of the outer cylinder towards the inner cylinder, and an end of each of the isolation strips away from a connecting end of each of the isolation strips connected to the outer peripheral wall of the inner cylinder and the inner peripheral wall of the outer cylinder is a movable end.

4. The test strip process device according to claim 2, wherein a third gap is formed between an end wall of each of the isolation strips towards the mounting cover and the end wall of the one end of the outer cylinder.

5. The test strip process device according to claim 3, wherein a distance between the movable end and the connecting end of each of the isolation strips gradually decreases along a direction towards the mounting cover, and a width of each of the isolation strips gradually decreases along the direction towards the mounting cover.

6. The test strip process device according to claim 1, wherein a sealing ring is provided at a side of the mounting wall of the mounting cover towards the inner cylinder, an outer diameter of the sealing ring gradually decreases along a direction away from the mounting cover, an outer diameter of the sealing ring at an end of the sealing ring away from the mounting cover is less than an inner diameter of the outer cylinder, the outer diameter of the sealing ring at a second end of the sealing ring close to the mounting cover is greater than the inner diameter of the outer cylinder, and an outer wall of the sealing ring abuts against an inner wall of the one end of the outer cylinder.

\* \* \* \* \*